United States Patent
Cable, II et al.

(10) Patent No.: US 11,779,457 B2
(45) Date of Patent: Oct. 10, 2023

(54) SYSTEMS TO AFFIX DEVICES TO INTRAOCULAR LENS ASSEMBLIES AND RELATED METHODS

(71) Applicants: SpyGlass Pharma, Inc., Aliso Viejo, CA (US); The Regents of the University of Colorado, A body corporate, Denver, CO (US)

(72) Inventors: Craig Alan Cable, II, Aliso Viejo, CA (US); Malik Y. Kahook, Denver, CO (US); Sean Maass, Aliso Viejo, CA (US); Rudolph Zacher, Aliso Viejo, CA (US)

(73) Assignees: SpyGlass Pharma, Inc., Aliso Viejo, CA (US); The Regents of the University of Colorado, a body Corporate, Denver, CO (US)

( * ) Notice: Subject to any disclaimer, the term of this patent is extended or adjusted under 35 U.S.C. 154(b) by 25 days.

(21) Appl. No.: 17/947,060

(22) Filed: Sep. 16, 2022

(65) Prior Publication Data
US 2023/0059430 A1 Feb. 23, 2023

Related U.S. Application Data

(63) Continuation of application No. PCT/US2022/038578, filed on Jul. 27, 2022.
(Continued)

(51) Int. Cl.
*A61F 2/16* (2006.01)

(52) U.S. Cl.
CPC .............. *A61F 2/1678* (2013.01); *A61F 2/167* (2013.01); *A61F 2/1691* (2013.01); *A61F 2002/1683* (2013.01);
(Continued)

(58) Field of Classification Search
CPC ... A61F 2002/1681-1683; A61F 9/0017; A61F 2250/0067-0068; A61F 2/167; A61F 2002/1683
See application file for complete search history.

(56) References Cited

U.S. PATENT DOCUMENTS

| | | | |
|---|---|---|---|
| 2005/0228401 A1 | 10/2005 | Zadno-Azizi et al. | |
| 2009/0130176 A1* | 5/2009 | Bossy-Nobs et al. | A61F 2/16 424/428 |

(Continued)

FOREIGN PATENT DOCUMENTS

GB 2586420 A 2/2021

OTHER PUBLICATIONS

Patent Cooperation Treaty, International Search Report and Written Opinion, International Application No. PCT/US2022/038578, date of mailing Nov. 7, 2022, 9 pages.

*Primary Examiner* — Rebecca S Preston
(74) *Attorney, Agent, or Firm* — Polsinelli PC

(57) ABSTRACT

Embodiments disclosed herein relate to systems and methods for securing a drug delivery component to an intraocular lens (IOL) assembly. The systems generally include a support base and a plunger. The support base includes a first portion configured to accommodate a drug delivery component; and a second portion configured to act as a plunger guide. The plunger can be inserted into the plunger guide such that the plunger is positioned to interface with a drug delivery component and an IOL assembly during use. The plunger includes an elongated body and a tip, wherein the tip can include a ramp configured to interface with a fixation loop of a drug delivery component during use and a compartment configured to interface with a haptic of an IOL assembly during use.

20 Claims, 12 Drawing Sheets

Related U.S. Application Data

(60) Provisional application No. 63/227,620, filed on Jul. 30, 2021.

(52) U.S. Cl.
CPC ... *A61F 2220/0025* (2013.01); *A61F 2240/001* (2013.01); *A61F 2250/006* (2013.01); *A61F 2250/0067* (2013.01)

(56) References Cited

U.S. PATENT DOCUMENTS

| | | |
|---|---|---|
| 2010/0074942 A1 | 3/2010 | Ratner et al. |
| 2015/0209274 A1 | 7/2015 | Venkatraman et al. |
| 2018/0353287 A1* | 12/2018 | Kudo .................. A61F 2/167 |
| 2020/0405538 A1 | 12/2020 | Mandell |

* cited by examiner

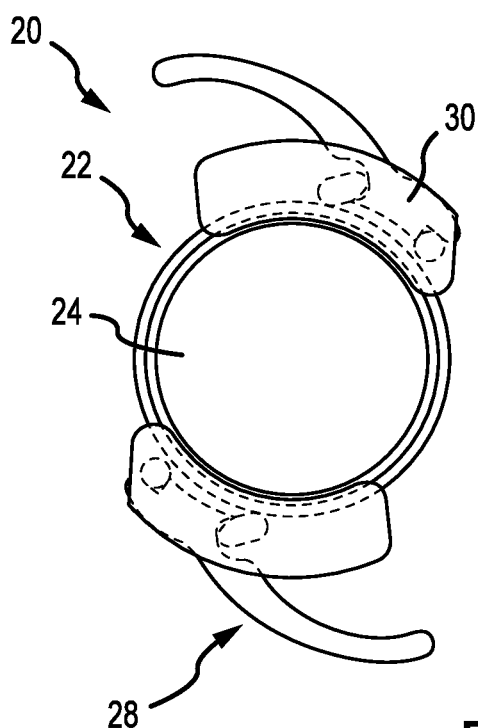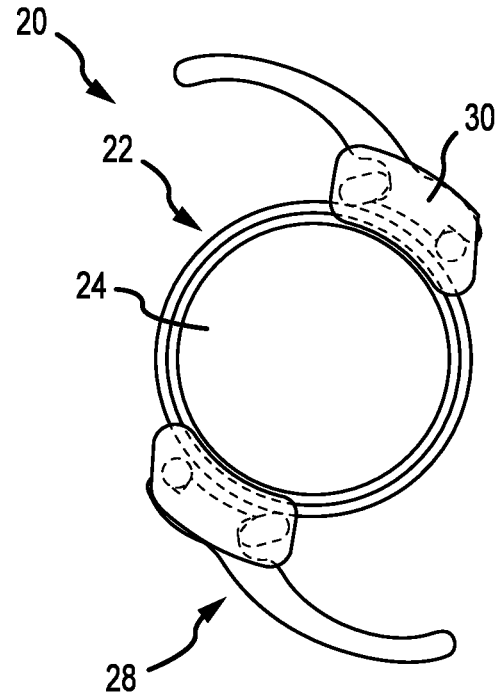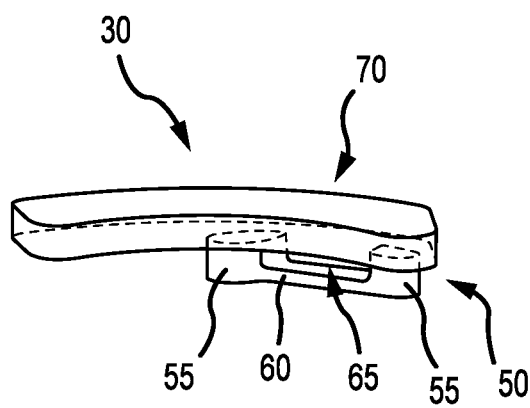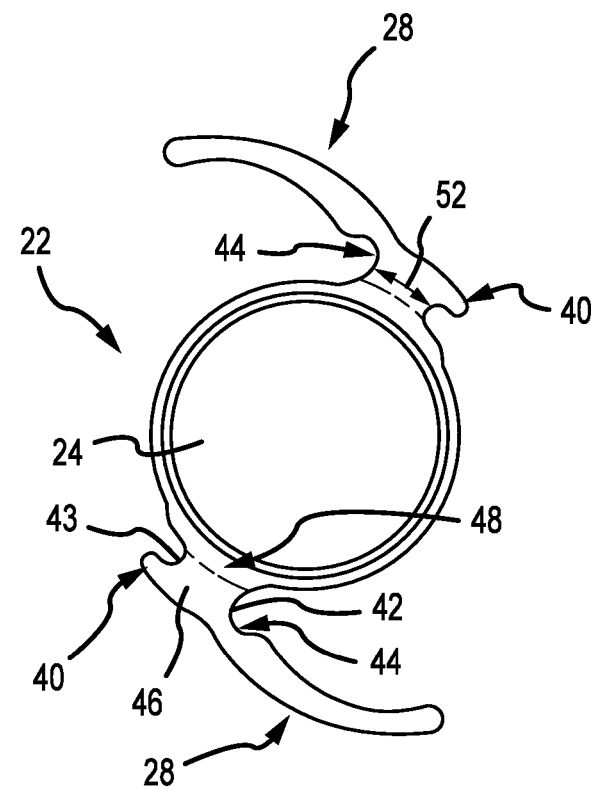
FIG.1A
FIG.1B
FIG.1C

SYSTEMS TO AFFIX DEVICES TO INTRAOCULAR LENS ASSEMBLIES AND RELATED METHODS

CROSS-REFERENCE TO RELATED APPLICATIONS

This application is a continuation of International Application No. PCT/US2022/038578, filed Jul. 27, 2022, which claims the benefit of U.S. Provisional Application No. 63/227,620, filed Jul. 30, 2021, each of which is incorporated herein by reference in its entirety for all purposes.

FIELD

The present disclosure relates to the field of intraocular drug delivery systems, and to systems for affixing drug delivery components to intralocular lens assemblies to create intraocular drug delivery systems and uses thereof.

BACKGROUND

Intraocular lenses (IOLs) are artificial lenses for the eye that can be implanted to replace the natural lens of a patient's eye after the natural lens is removed. By way of example, a patient's natural lens can be removed because it is affected by cataracts, and an IOL can be implanted to provide clear vision and some degree of focusing to the patient. An intraocular lens can also be implanted in a patient without removing the natural lens (a phakic intraocular lens or PIOL), to correct extreme near-sightedness or far-sightedness.

For example, it can be advantageous to administer therapeutic agents to the eye, coincident with implantation of the IOL, to alleviate various side effects of the IOL or treat other conditions of the eye that might coexist with the conditions that lead to, for example, cataracts and glaucoma. Existing conditions or side-effects of introduction of an IOL such as infection and inflammation can be treated with therapeutic agents incorporated into an IOL or other devices that can be secured to the IOL. In addition to IOLs, ocular implants not including lenses can be implanted to address various conditions.

Previous attempts have disclosed various configurations of drug delivery components to be used in conjunction with IOLs, including the placement of drug delivery components on haptics of IOLs. The systems and methods described below provide for more efficient and/or robust approaches for securing a drug delivery component to an IOL.

SUMMARY

Certain aspects of the present disclosure can include systems for securing one or more drug delivery component to an intraocular lens (IOL) assembly. In accordance with these aspects, the drug delivery component can include a therapeutic agent-containing portion and a fixation loop coupled to the therapeutic agent-containing portion. In certain embodiments, the therapeutic agent-containing portion can be a drug-containing portion. In accordance with these embodiments, the therapeutic agent-containing portion can be a pad, a sponge, a matrix or other component capable of harboring and dispersing one or more therapeutic agents. In yet other embodiments, the therapeutic agent containing portion can further include another agent for harboring or storing the therapeutic agent for distribution (e.g., a solid matrix, semi-solid matrix, a gel, hydrogel or other material capable of storing a therapeutic for long-term or short-term distribution). The IOL assembly can include at least one haptic. In certain aspects, the system can include a plunger and a support base. The plunger can include an elongated body and a tip. The support base can include at least a first portion and a second portion. The first portion can accommodate the drug delivery component. The second portion can include a plunger guide configured for guiding movement of the plunger relative to the support base. When the drug delivery component is positioned at the first portion, the plunger is configured to be guided in distal movement by the plunger guide such that the tip is received in the fixation loop of the drug delivery component to secure the drug delivery component in a first state at the first portion.

In certain embodiments, upon the tip of the plunger being received in the fixation loop, additional distal movement of the plunger is configured to transition the fixation loop to a second state with the fixation loop being expanded.

In certain embodiments, the tip of the plunger includes a top surface and a ramp extending upwards from the top surface, the ramp configured to expand the fixation loop of the drug delivery component during distal movement into the second state.

In certain embodiments, the ramp includes a proximal surface, the tip of the plunger further including a sidewall extending proximally from the proximal surface of the ramp, wherein the proximal surface of the ramp, the sidewall, and the top surface of the tip of the plunger define a compartment for receiving a haptic of the IOL assembly therein and through the fixation loop in the second state.

In certain embodiments, when the haptic of the IOL assembly is received in the compartment, proximal retraction of the plunger is configured to transition the fixation loop to a third state with the fixation loop being contracted onto the haptic of the IOL assembly.

In certain embodiments, the first portion includes a recess sized and shaped to receive the therapeutic agent-containing component of the drug delivery component therein.

In certain embodiments, the first portion includes an IOL recess sized and shaped to receive the IOL assembly therein.

In certain embodiments, the plunger guide includes a passageway (or channel) for guiding movement of the plunger.

In certain embodiments, the system further includes a key lock configured to interface with the plunger to inhibit or cease movement within the plunger guide.

In certain embodiments, the system further includes the drug delivery component.

Aspects of the present disclosure can include a method for securing a drug delivery component to an intraocular lens (IOL) assembly. The drug delivery component can include a therapeutic agent-containing component and a fixation loop coupled to the therapeutic agent-containing component. The IOL assembly can include a haptic. The method can include the following steps. Providing a system including a support base and a plunger where the plunger includes a tip. The support base can include a first portion and a second portion. The first portion can accommodate the drug delivery component. The second portion can include a plunger guide configured for guiding movement of the plunger relative to the support base. The method can further include inserting the drug delivery component posterior-side up at the first portion of the support base such that the fixation loop of the drug delivery component is exposed. The method can further include advancing the tip of the plunger through the fixation loop of the drug delivery component so as to expand the fixation loop. The method can further include feeding the haptic of the IOL assembly through the fixation loop of the drug delivery component. The method can further include retracting the tip of the plunger through the fixation loop of the drug delivery component so as to contract the fixation loop onto the haptic.

In certain embodiments, the method can further include positioning the IOL assembly posterior-side up in the support base.

In certain embodiments, feeding the haptic of the IOL assembly through the fixation loop of the drug delivery component can further include at least one of the following using forceps, grasping the haptic and feeding a first end of the haptic through the fixation loop of the drug delivery component.

In certain embodiments, the method can further include pulling on the first end of the haptic until a second end of the haptic is seated against a ramp of the tip of the plunger.

Certain aspects of the present disclosure can include a system for securing a drug delivery component to an intraocular lens (IOL) assembly. The drug delivery component can include a therapeutic agent-containing component and a fixation loop coupled to the therapeutic agent-containing component. The IOL assembly can include a haptic or more than one haptic. The system can further include a support base and a plunger. The support base can include a plunger guide and a recess with the recess being sized and shaped to receive the therapeutic agent-containing component of the drug delivery component therein in a posterior-side up orientation. The plunger guide can guide movement of the plunger relative to the support base along an axis that intersects the recess. When the therapeutic agent-containing component is received in the recess, the plunger is configured to be guided in distal movement by the plunger guide such that a tip of the plunger is received in the fixation loop of the drug delivery component.

In certain embodiments, the tip of the plunger includes a ramp and a sidewall extending proximally from the ramp.

In other embodiments, a compartment is formed by a proximal surface of the ramp and an inner surface of the sidewall, the compartment sized and shaped to receive a portion of a haptic therein.

In certain embodiments, in the posterior-side up orientation, the fixation loop is exposed.

In certain embodiments, upon the tip of the plunger being received in the fixation loop of the drug delivery component, additional distal movement of the plunger is configured to expand the fixation loop for receiving the haptic of the IOL assembly therethrough.

In certain embodiments, the system can include the drug delivery component according to disclosures herein. In other embodiments, kits are contemplated to include any or all components disclosed regarding systems described herein. In some embodiments, kits can include some or all components of systems disclosed and optionally, one or more instruction guide. In one embodiment, an IOL can be provided separately from a system disclosed herein. In other embodiments, an IOL is provided within a kit containing a system disclosed herein.

BRIEF DESCRIPTION OF THE DRAWINGS

FIGS. 1A-1C illustrate an exemplary IOL assembly and drug delivery component that can be used in connection with the systems and methods of the disclosure. FIG. 1A illustrates two intraocular drug delivery systems, each including drug delivery components affixed to the haptics of an IOL assembly. FIG. 1B illustrates an exemplary drug delivery component, and FIG. 1C illustrates an exemplary IOL assembly.

FIG. 3A shows a top view of the plunger. FIG. 3B shows a perspective side view of the plunger.

FIG. 3C shows a front perspective view. FIG. 3D shows a side perspective view.

DETAILED DESCRIPTION

Figure 2A:
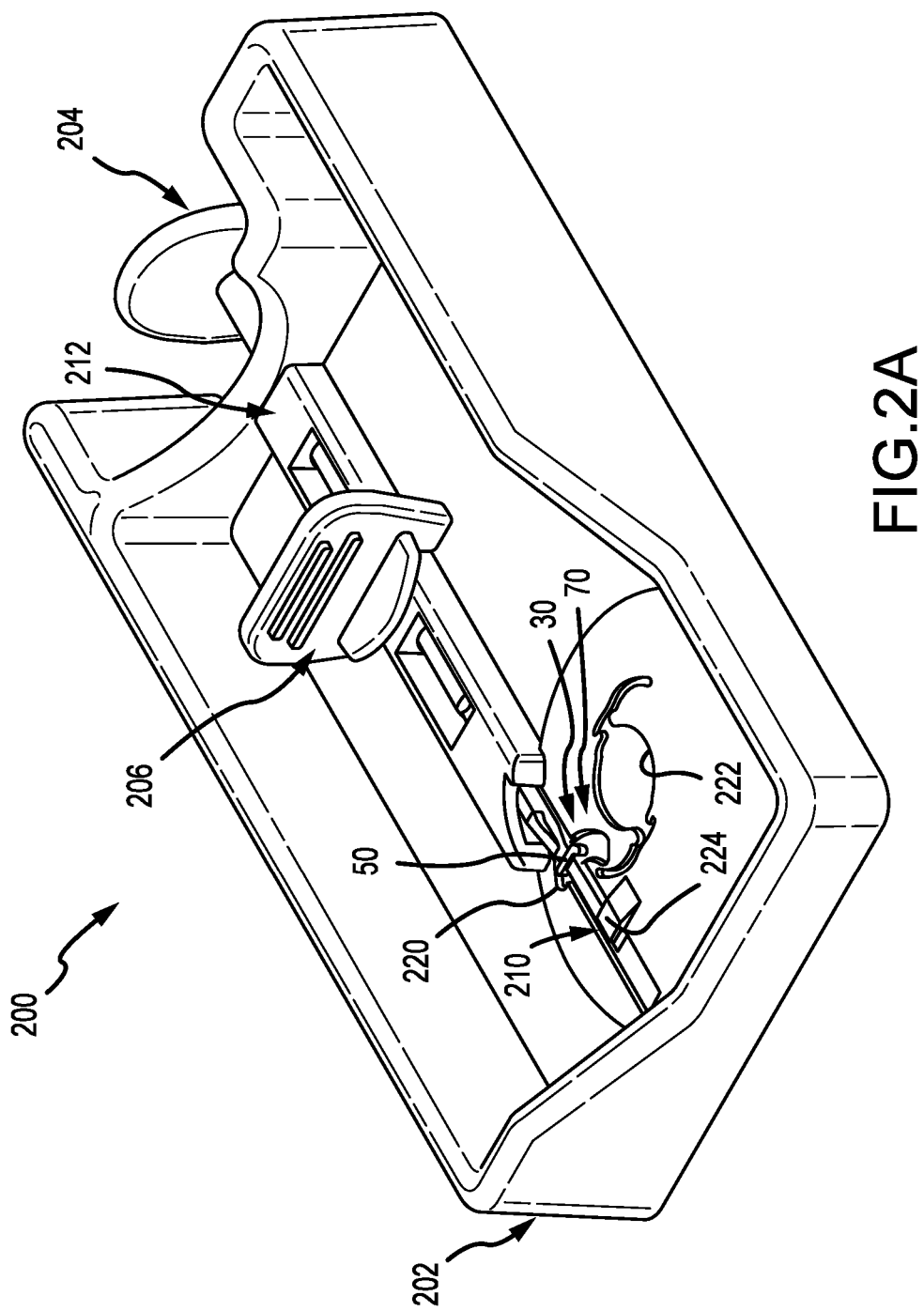
FIGS. 2A and 2B illustrate two perspective views of a system for affixing a drug delivery component to an IOL assembly, in accordance with embodiments of the disclosure.

The present disclosure relates to systems for affixing or securing drug delivery components to intraocular lens (IOL) assemblies and related methods of use.

For context, FIGS. 1A-1C illustrate exemplary intraocular drug delivery systems 20 that can be assembled using the systems and methods of the disclosure. Such intraocular drug delivery systems 20 can include an IOL assembly 22 and one or more drug delivery components 30. The IOL assembly 22 includes an optic/lens 24 at the center and one or more haptics 28 extending outwardly from the plane of optic/lens 24 or a parallel plane. The optic/lens 24 can include an optic with vision correction; or can be a scaffold for providing structural support. The drug delivery component 30 is configured for attachment to a haptic 28 of the IOL assembly 22. In certain embodiments, the attachment is releasable. In other embodiments, the attachment is not releasable. The intraocular drug delivery system 20 includes an anterior surface and a posterior surface, relative to the eye of the subject when implanted. In some embodiments, the intraocular drug delivery system 20 can optionally include other devices such as a capsular tension ring, or a capsular scaffold for holding the system in place during use.

The outward extent of the haptic 28 is long enough to impinge on the capsular bag of the eye of the subject when the system 20 is implanted, while the radially outward extent of the drug delivery component 30, when installed on the implanted IOL assembly 22, is preferably shorter than that of the haptic 28, to avoid impingement of the drug delivery component 30 on the capsular bag in the equatorial region of the capsular bag of the eye of the subject. In certain embodiments, the drug delivery component 30 can be configured to dimensionally correspond to the size and shape of the optic-haptic junction area. In other embodiments, the drug delivery component 30 is configured to be dimensionally larger than the optic-haptic junction area. However, the disclosure is not so limited, and the drug delivery component 30 can be sized as shaped in any manner suitable for the intended use, e.g., one-quarter around the circumference of the optic, one-third around the circumference of the optic, one-half around the circumference of the optic, etc.

FIG. 1A illustrates two intraocular drug delivery systems 20. On the left, the system 20 includes a pair of larger drug delivery components 30. On the right, the system 20 includes a pair of relatively smaller drug delivery components 30. The larger drug delivery components 30 can, for example, elute therapeutic agents for a longer duration or at a higher rate compared to the smaller drug delivery components 30. The drug delivery components 30 can include different properties as well, such as different rates of elution, different therapeutic agents, and other aspects that can be modified. The present disclosure illustrates the relatively larger drug delivery component 30 shown on the left of FIG. 1A. However, the disclosure is not so limited, and the systems and methods described herein are also applicable to the relatively smaller drug delivery component 30 shown on the right of FIG. 1A.

FIG. 1B illustrates an exemplary drug delivery component 30 of the disclosure. The drug delivery component 30 can include a therapeutic agent, which can include the entirety of drug delivery pad 70, or a portion thereof (such as an interior drug delivery pad, gel, or drug eluting matrix). The drug delivery component 30 can include a drug delivery pad 70, which can elute the therapeutic agent from a drug depot, or dissolve or biodegrade over time to release the therapeutic agent or be formulated in any other suitable drug delivery configuration known in the art to deliver the therapeutic agent. Drug delivery component 30 can further include fixation portion 50 affixed to the posterior side of the drug delivery pad 70. A drug delivery component 30, including a drug delivery pad 70, can be referred to as a therapeutic agent-containing portion, drug-containing portion, or drug portion. A therapeutic agent-containing portion as referenced above can be a pad, a sponge, a matrix, or other component capable for harboring, storing, and/or dispersing one or more therapeutic agents. The fixation portion 50 (also referred to as fixation loop) can include structures 55 such as posts which extend vertically from the posterior side of drug delivery pad 70 and are connected by a horizontally extending band 60 to form an opening 65 (e.g., a slot, aperture, or compartment). The opening 65 is configured to receive the haptic 28 of an IOL assembly 22, such that the haptic 28 can pass through the opening 65. The fixation portion 50 can generally function as a drug delivery component 30 retention loop, and can be formed from any suitable materials for the intended use. The fixation loop 50 can be flexible to stretch or expand in order for the haptic 28 of the IOL assembly 22 to be received through the loop 50. And, once expanded and in position over the optic-haptic junction, the fixation loop 50 can be contracted over the optic-haptic junction. By way of non-limiting example, the fixation portion 50 can be formed from FDA-approved polymers for ophthalmic use that are compatible with the intended therapeutic agents, e.g., medical grade silicone. Further, the fixation portion 50 can be attached to the drug delivery pad in any method known in the art suitable for such purposes, e.g., medical grade adhesives, thermal bonding, etc.

In certain embodiments, as illustrated in FIG. 1C, the haptic 28 of the IOL assembly 22 can be configured with features to retain and stabilize the drug delivery component 30 relative to the IOL assembly 22. To that end, the haptic 28 includes a retention tab 40 and a gusset 44, which together form a waist or in-cut portion 52 for retaining and stabilizing the fixation portion 50 of the drug delivery component 30 when the fixation loop 50 is received in the waist portion 52. The waist portion 52 defines a narrow portion which widens towards the optic/lens 24 and also widens towards the gusset 44 and retention tab 40. In this way, the drug delivery component 30 is retained at the waist portion 52.

Still referring to FIG. 1C, the retention tab 40 at an optic end or first end of haptic 28 has an outer surface 43 and an inner surface 42 at the optic-haptic junction 48. Opposite the outer surface 43 formed by retention tab 40, the haptic 28 includes a curvilinear notch or gusset 44 having the inner surface 42 that facilitates flexing and bending of the haptic 28 during use. The waist portion 52 is defined between the inner surface 42 and the outer surface 43 of the haptic 28. In some embodiments, the outer surface 43 of the retention tab 40 includes a radial surface and the inner surface 42 of the retention tab at the gusset 44 includes a radial surface so as to provide a curved inner portion at the junction of the haptic 28 to the lens 24. Between retention tab 40 and gusset 44, the anterior surface of haptic 28 provides an upper surface 46 which can interface with at least a portion of drug delivery component 30 to stabilize its orientation during use. In some embodiments, upper surface 46 can be sized and shaped to match the size and shape of the drug delivery component 30 (e.g., interface with the entire drug delivery component 30 or substantially the entire drug delivery component 30).

Figure 2B:
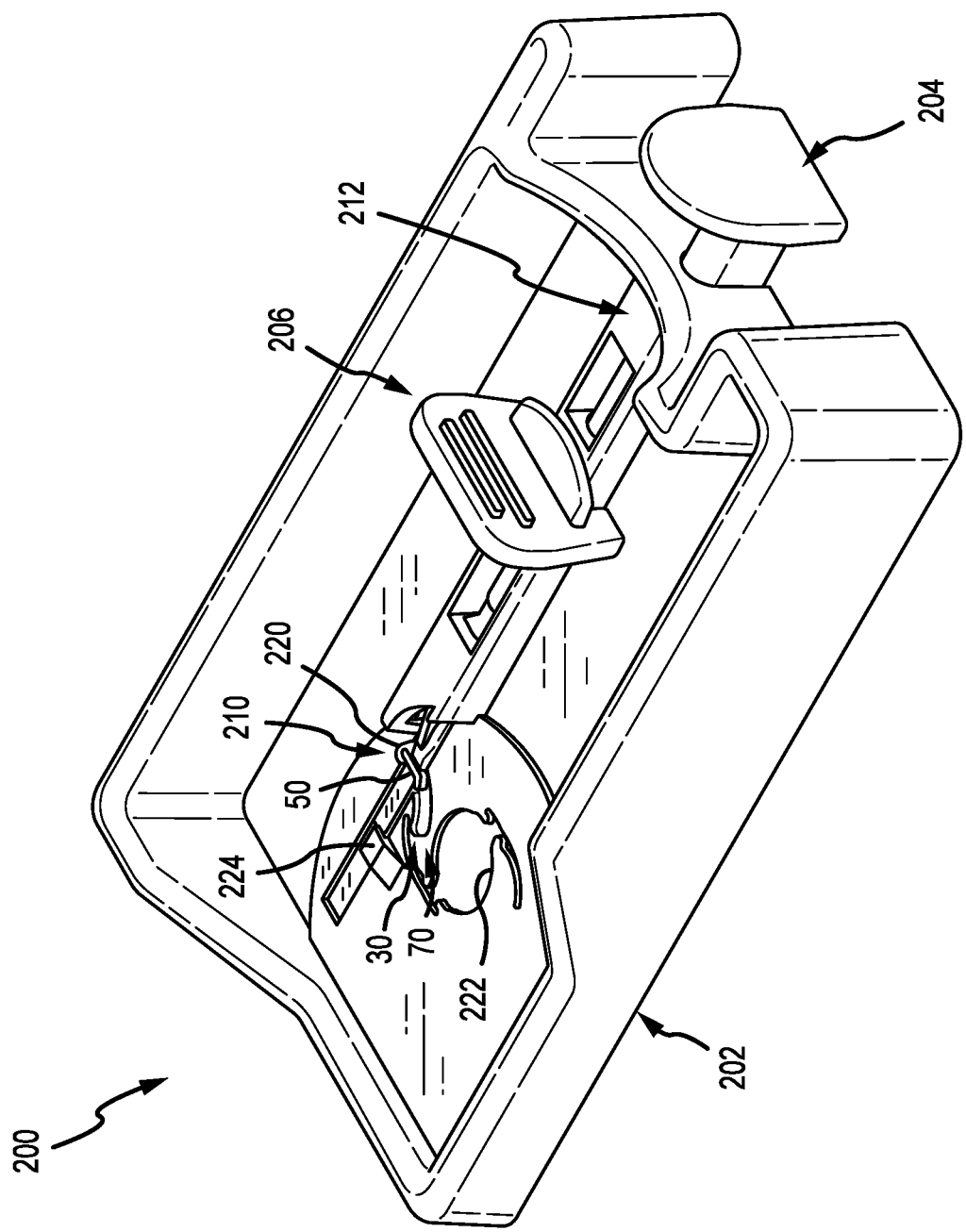
Figure 2C:
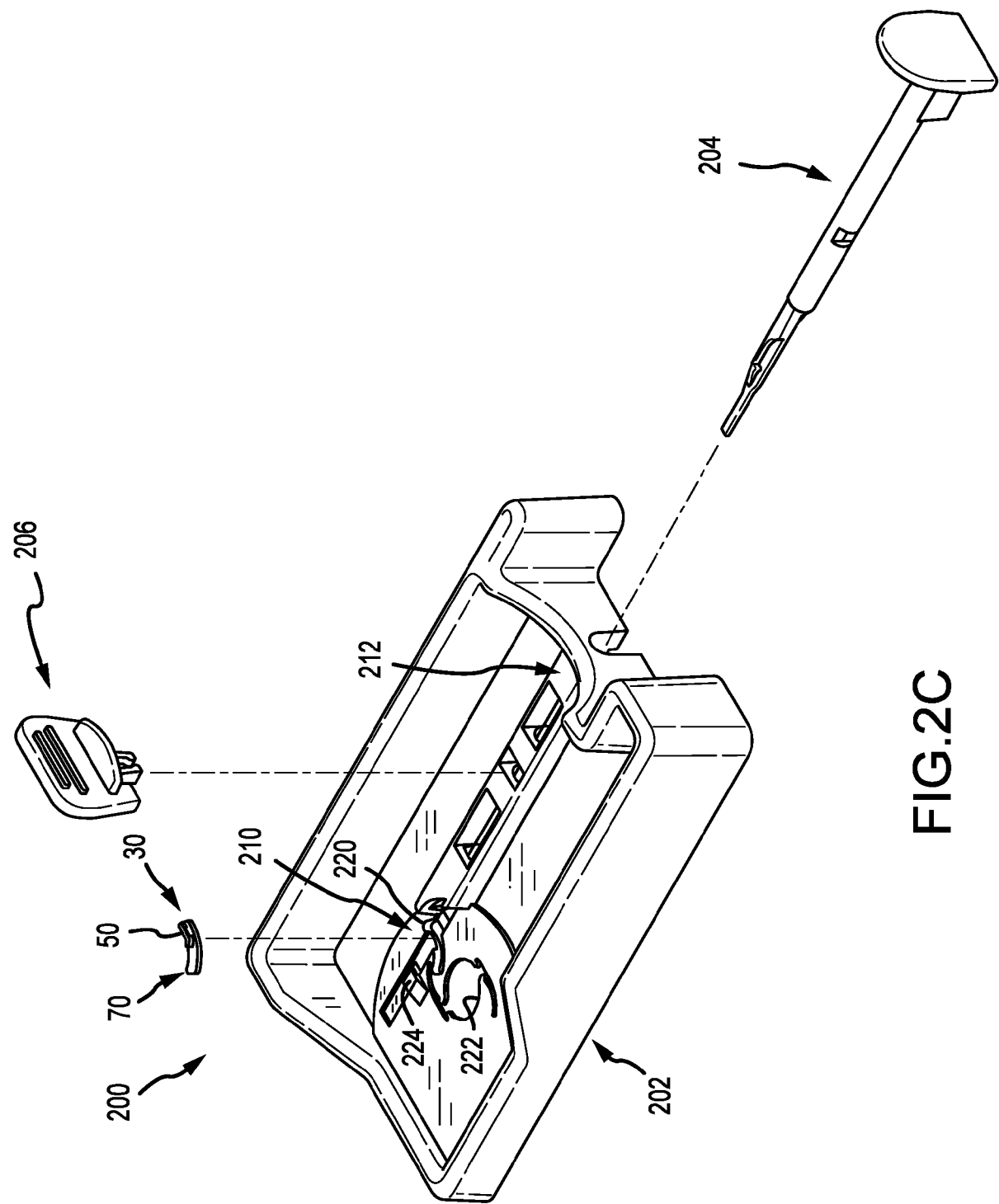
FIG. 2C illustrates an exploded perspective view of the system of FIGS. 2A and 2B, in accordance with embodiments of the disclosure.

With reference to FIGS. 2A through 2C, system 200 of the disclosure generally includes a support base or tray 202 and a plunger 204. The system 200 can optionally include a plunger stop/lock pin or key 206 to hold the plunger 204 in place prior to use, if desired. In certain embodiments, the support base 202 includes a first portion 210 forming a slot, groove, recess, or other impression 220 sized and shaped to accommodate or receive a drug delivery component 30 in a posterior-side up orientation to expose the fixation loop 50. The first portion 210 can also include a slot, groove, recess, or other impression 222 sized and shaped to accommodate or receive an IOL assembly (not shown in FIGS. 2A through 2C) in a posterior-side up orientation. The IOL assembly can be placed into the recess 222 to exhibit the correct orientation of the IOL to couple the IOL assembly to the drug delivery component 30. In other embodiments, instead of a recess 222, the first portion 210 can include protrusions that are sized and shaped to receive an IOL assembly and exhibit the correct orientation of the IOL. The support base 202 also includes a second portion including a plunger guide 212, wherein the plunger 204 is inserted into the plunger guide 212 along an axis that intersects the recess 220 for the drug delivery component 30. In this way, the plunger 204 is positioned to interface with a drug delivery component 30 and IOL assembly (not shown) during use. In some embodiments, the plunger 204 can be guided by the plunger guide 212 in distal movement (i.e., towards the recess 220) and in proximal movement (i.e., away from the recess 220). In distal movement, the plunger 204 can extend through the fixation loop 50 of the drug delivery component 30, which is shown in FIGS. 2A and 2B. In this state, the tip of the plunger 204 can be positioned underneath a tab 224 to inhibit the plunger 204 from movement away from the surface of the support base 202. The plunger guide 212 can be a passageway that receives the plunger 204 along a linear path or axis.

As illustrated in FIGS. 2A and 2B, the key 206 is insertable into an opening in the plunger guide 212. As will be described subsequently, the key 206 includes features that interface with the plunger 204 and the plunger guide 212 to inhibit distal and proximal movement of the plunger 204. FIGS. 2A and 2B illustrate a state of the system 200 with the key 206 locking the plunger 204 in position relative to the support base 202. The system 200, in this state, is suitable for packaging and shipping.

Figure 3A:
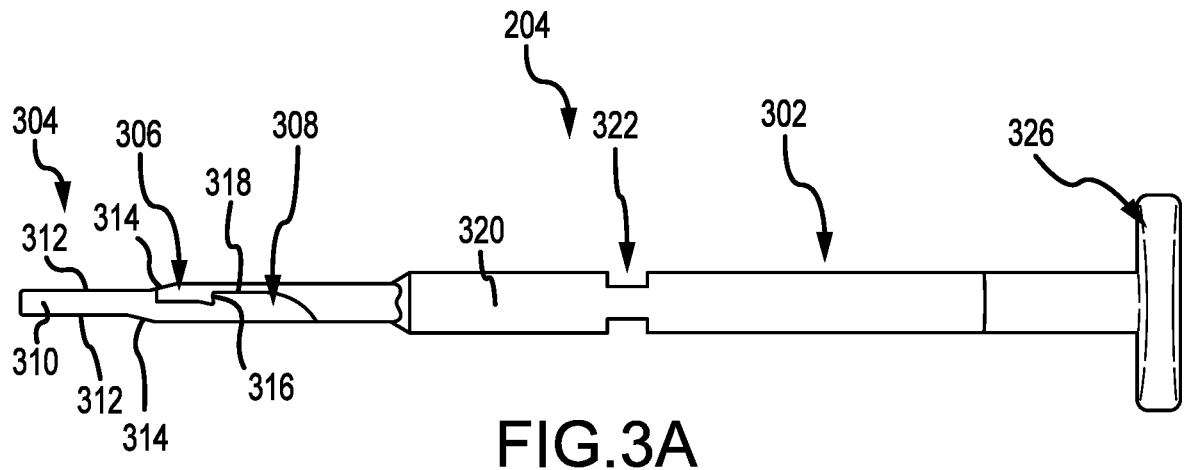
FIGS. 3A and 3B illustrate an exemplary plunger, in accordance with embodiments of the disclosure.
Figure 3B:
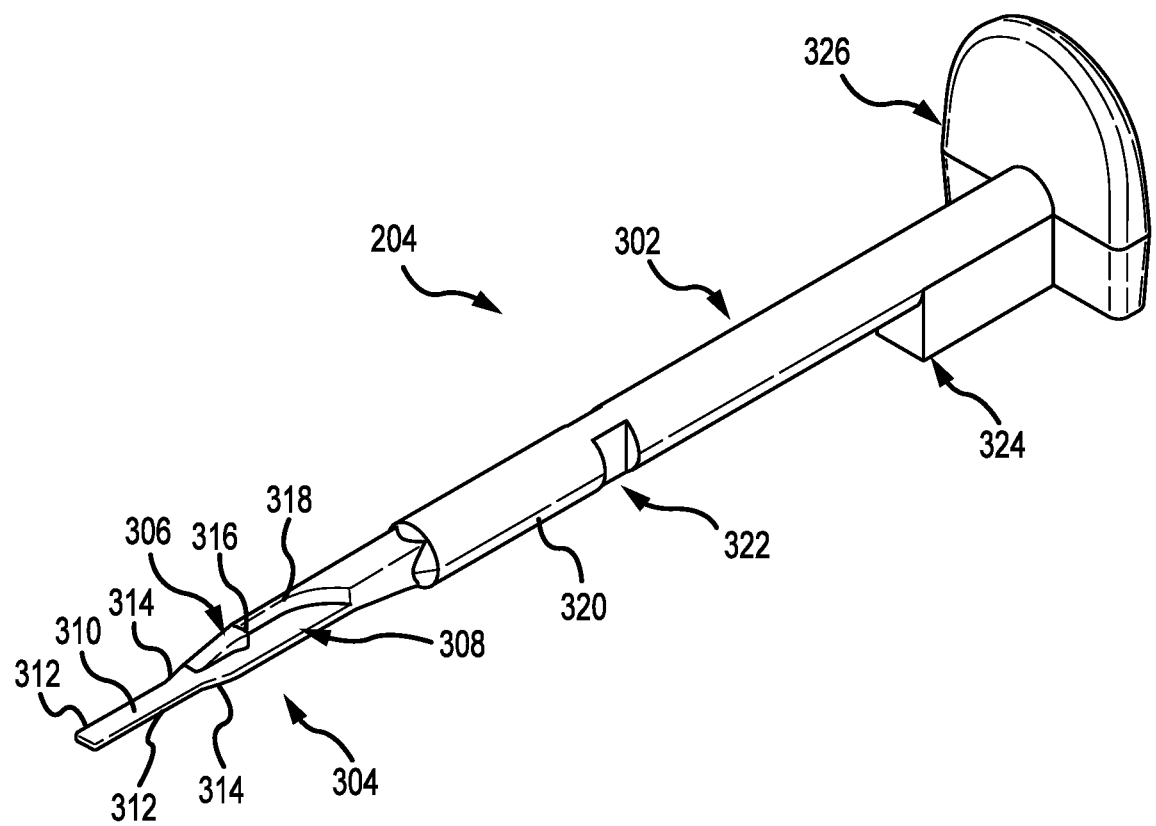
Figure 3C:
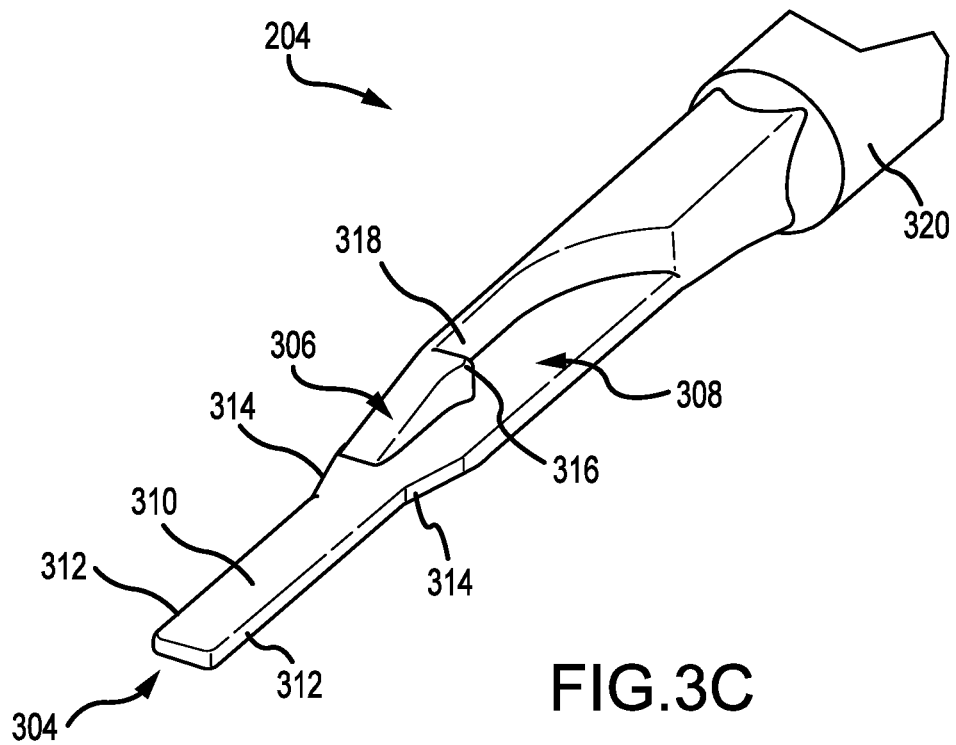
FIGS. 3C and 3D illustrate partial close-up view of a plunger tip, in accordance with embodiments of the disclosure.
Figure 3D:
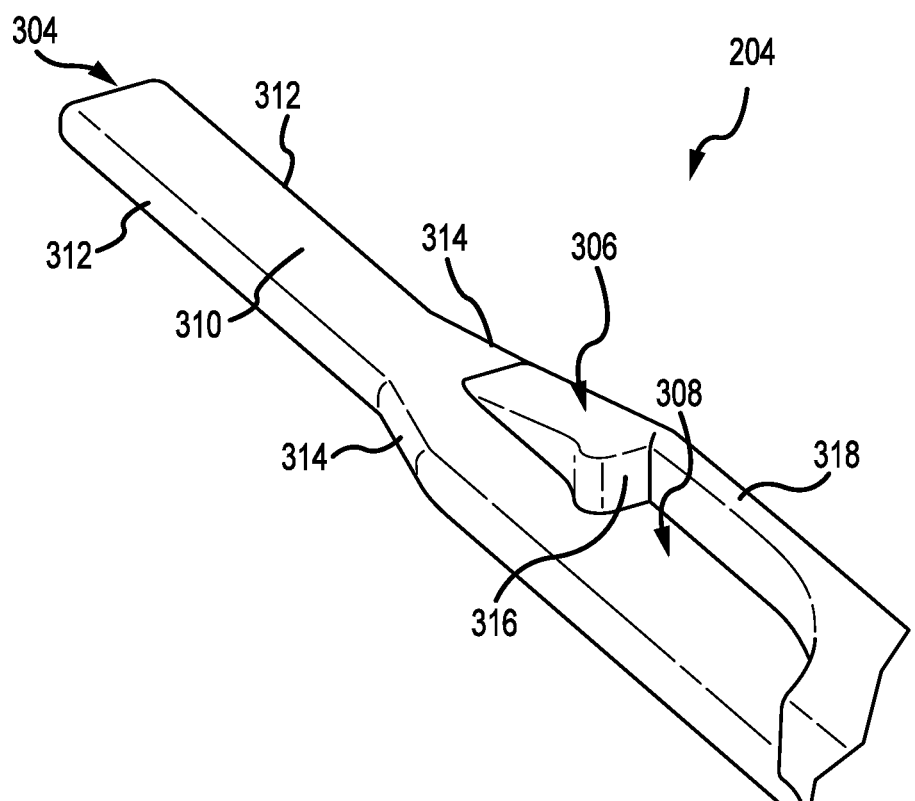

With reference to FIGS. 3A and 3B, the plunger 204 includes an elongated body 302 and a tip 304 at a distal end thereof. The plunger tip 304 includes a ramp 306 configured to interface with the fixation loop of the drug delivery component (not shown in FIGS. 3A and 3B) during use, and a compartment 308 configured to interface with the haptic of the IOL assembly (not shown) during use. FIGS. 3C and 3D show partial close-up views of tip 304, including ramp 306 and compartment 308.

Still referring to FIGS. 3A through 3D, the plunger tip 304 includes a top surface 310 that is generally planar. Extending proximally from the most distal point, the plunger tip 304 includes a pair of generally parallel side edges 312. Each of the pair of side edges 312 include angled sections 314 that extend outward such that the width of the plunger tip 304 widens. As seen in the figures, one of the angled sections 314 extends outward more distally than the other angled section 314. The ramp 306 is defined on a part of the top surface 310 of the plunger tip 304. That is, the width of the ramp 306 does not extend across the entirety of width of the top surface 310. Stated differently, there is an opened space or gap where the top surface 310 continues past the ramp 306 on one side thereof. A proximal side of the ramp 306 includes a proximal surface 316 and is generally planar. A thin sidewall 318 extends proximally from one of the side edges 312. As it extends proximally, the thin sidewall 318 widens and arcs to the opposite side edge 312. The compartment 308 is defined between the proximal surface 316, the sidewall 318, and the top surface 310 of the plunger tip 304. The compartment 308 is coextensive with the opened space or gap where the top surface 310 continues past the ramp 306.

Proximally to the plunger tip 304, the plunger 204 includes a shaft 320 that is generally cylindrical. The shaft 320 includes a pair of notches 322 that extend downward through opposite portions of the cylindrical shaft 320. The pair of notches 322 are sized and shaped to interface with the key 206. At the proximal end of the plunger, 204 is an alignment structure 324 and an engagement structure 326 sized and shaped to be engaged by the user (e.g., thumb).

Figure 4A:
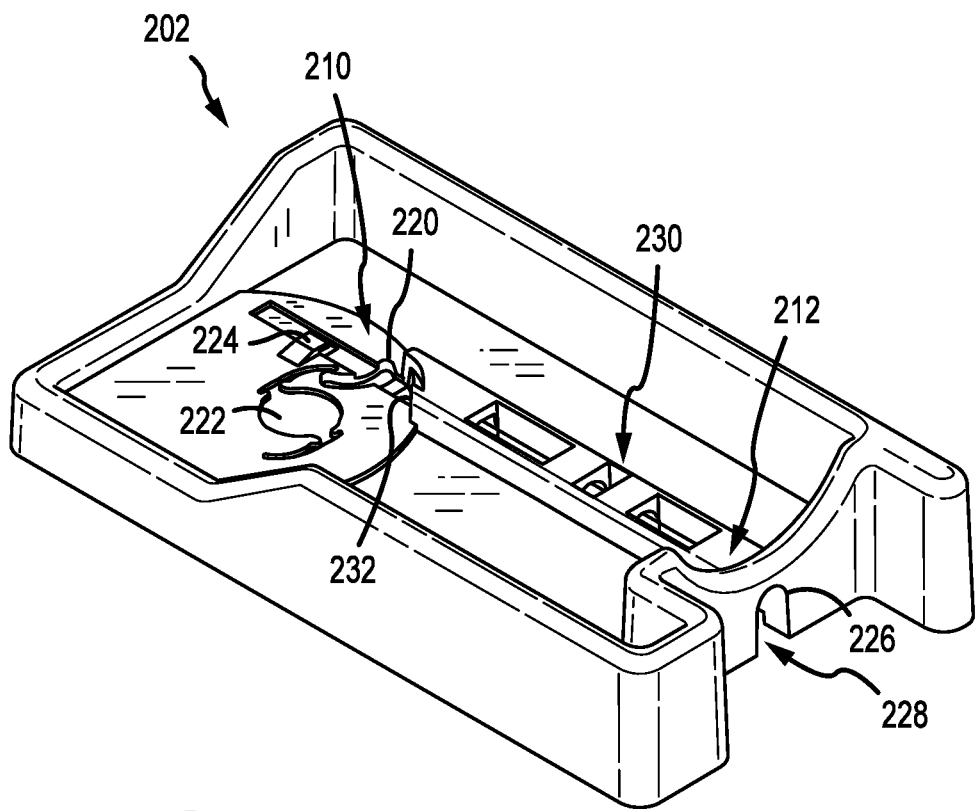
FIGS. 4A and 4B illustrate, respectively, a perspective view and a top view of a support base or tray of the system for affixing a drug delivery component of an IOL assembly, in accordance with embodiments of the disclosure.
Figure 4B:
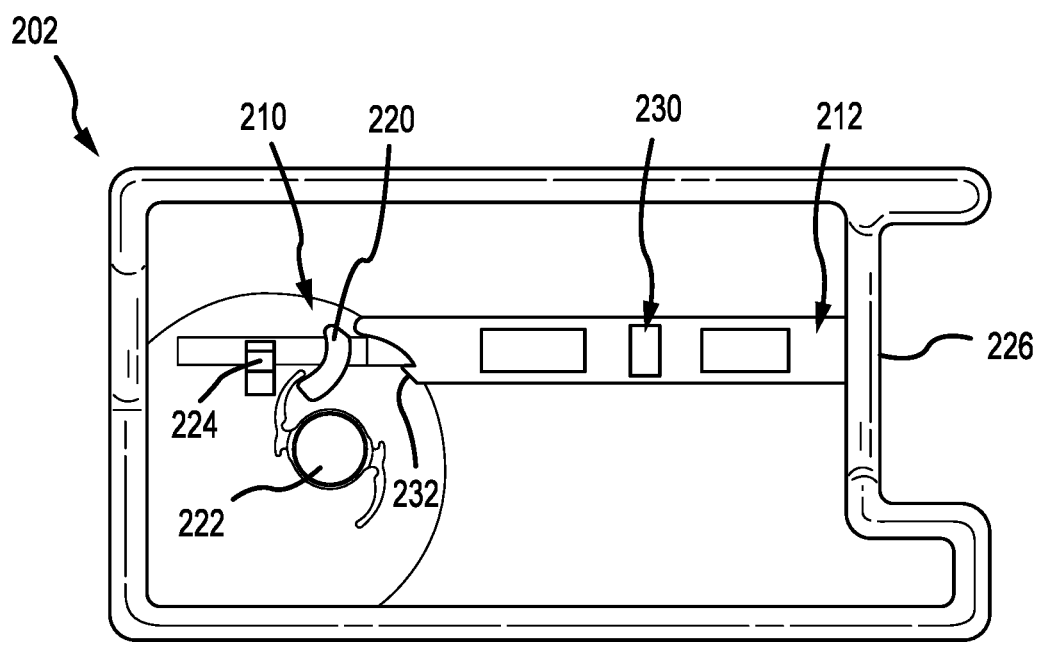

FIGS. 4A and 4B illustrate, respectively, a perspective view and a top view of the support base 202. As seen in the figures, the support base 202 includes the first portion 210 forming a slot, groove, recess, or other impression 220 sized and shaped to accommodate or receive a drug delivery component (not shown in FIGS. 4A and 4B) in a posterior-side up orientation to expose the fixation loop. Adjacent the recess 220 of the drug delivery component is the recess 222 for receiving the IOL assembly (not shown). As illustrated in the figures, the recess 222 for the IOL assembly does not intersect the recess 220 of the drug delivery component. The recess 222 is oriented as a guide that the user can use when coupling the drug delivery component to the haptic of the IOL assembly. For example, the user can place the IOL assembly into the recess 222 to illustrate the correct orientation of the IOL before coupling the IOL assembly to the drug delivery component. At the first portion 210 is a tab 224 for interfacing with the plunger tip of the plunger (not shown).

The plunger guide 212 includes a passageway from the proximal end of the support base 202 that is sized to receive the plunger therein in a single orientation. The proximal opening 226 of the support base 202 includes an elongated section 228 that is sized and shaped to fit the alignment structure of the plunger in an orientation that aligns the ramp on the plunger tip in an upwards position. In this orientation, the notches on the plunger are aligned in an opening 230 in the plunger guide 212 such that the key (not shown) can be inserted in the opening 230 and secured to the plunger at the notches. As illustrated in the figures, the distal end of the plunger guide 212 includes an arcuate surface that terminates in an angled corner 232. The angled corner 232 is sized and shaped to interface with the haptic of the IOL assembly and support it in place when the plunger is retracted (moved proximally) to contract the fixation loop of the drug delivery component onto the haptic.

Figure 5A:
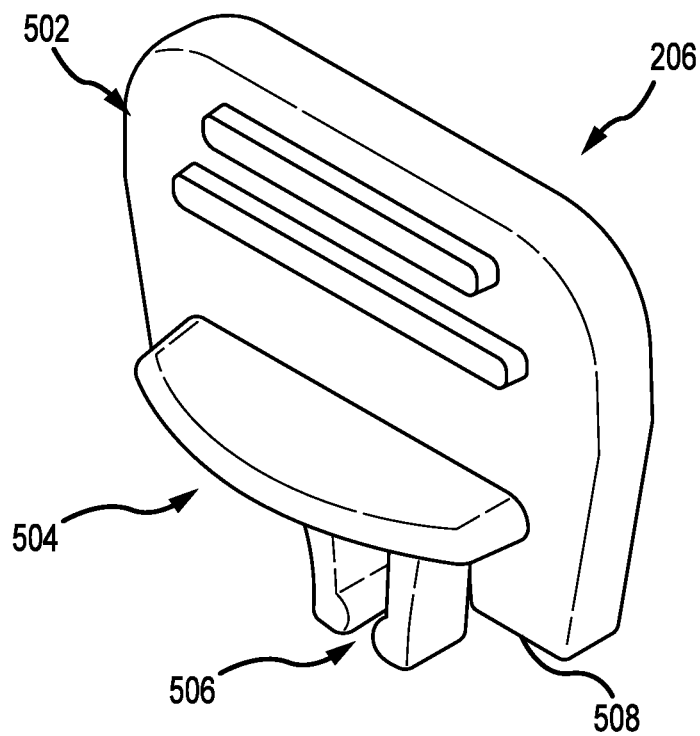
FIGS. 5A and 5B illustrate, respectively, a perspective view and a front view of a key of the system for affixing a drug delivery component of an IOL assembly, in accordance with embodiments of the disclosure.
Figure 5B:
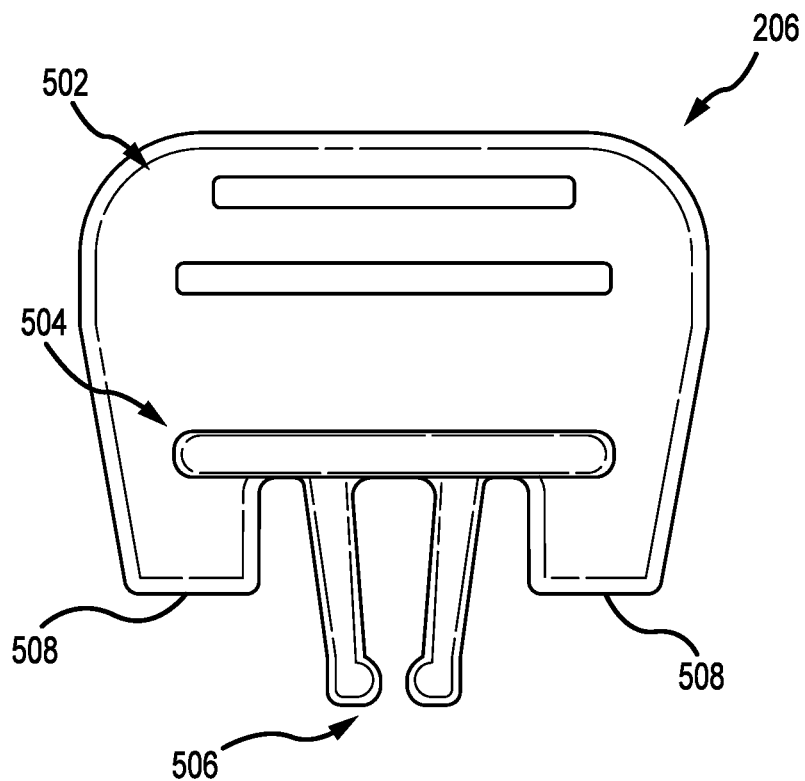

FIGS. 5A and 5B illustrate, respectively, a perspective view and a front view of the key 206 of the system for affixing a drug delivery component of an IOL assembly. As illustrated in the figures, the key 206 includes an engagement structure 502 in the form of a tab or plate at the proximal end. At an approximate midpoint of the key 206 is a guard 504 extending outward from the engagement structure 502. Extending distally from the guard 504 is a pair of fingers 506 sized and shaped to be received around the shaft of the plunger at the notches (not shown in FIGS. 5A and 5B). The engagement structure 502 extends downwards from the guard 504 on two sides and terminates at a pair of ends 508 that engage with the plunger guide.

Figure 6A:
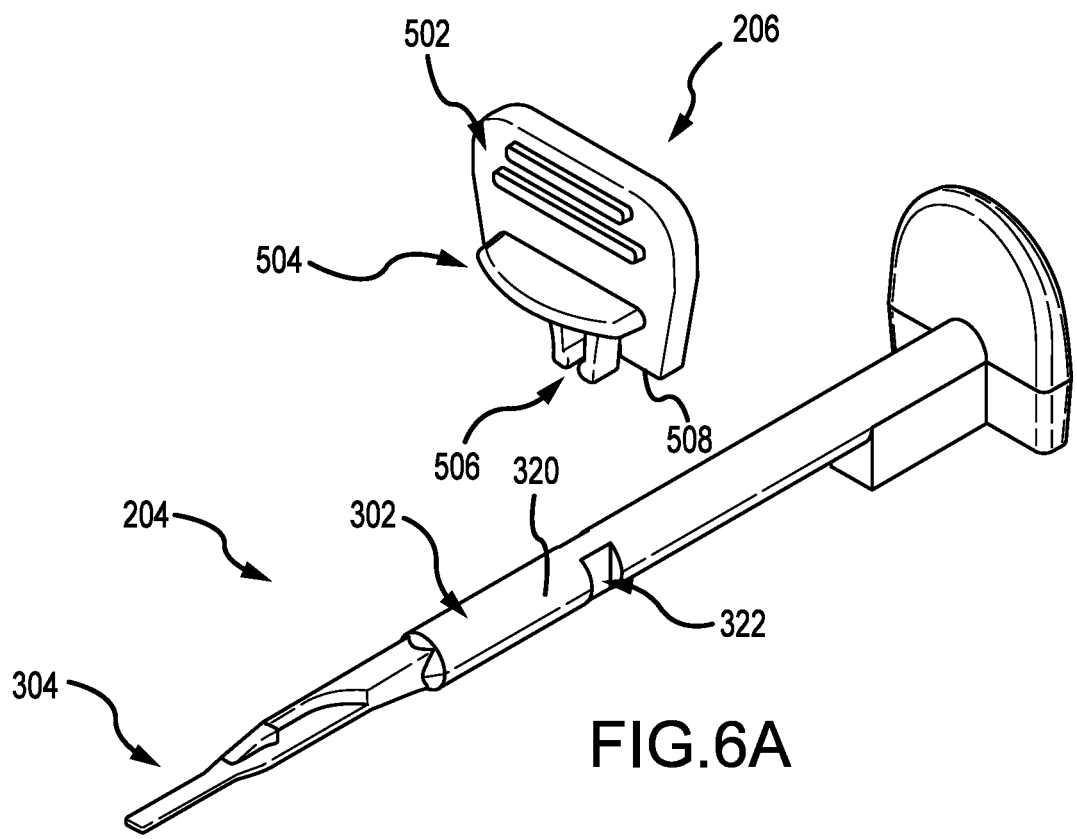
FIGS. 6A and 6B illustrate, respectively, a perspective view of the key and the plunger positioned apart from each other, and a perspective view of the key coupled to the plunger, in accordance with embodiments of the disclosure.
Figure 6B:
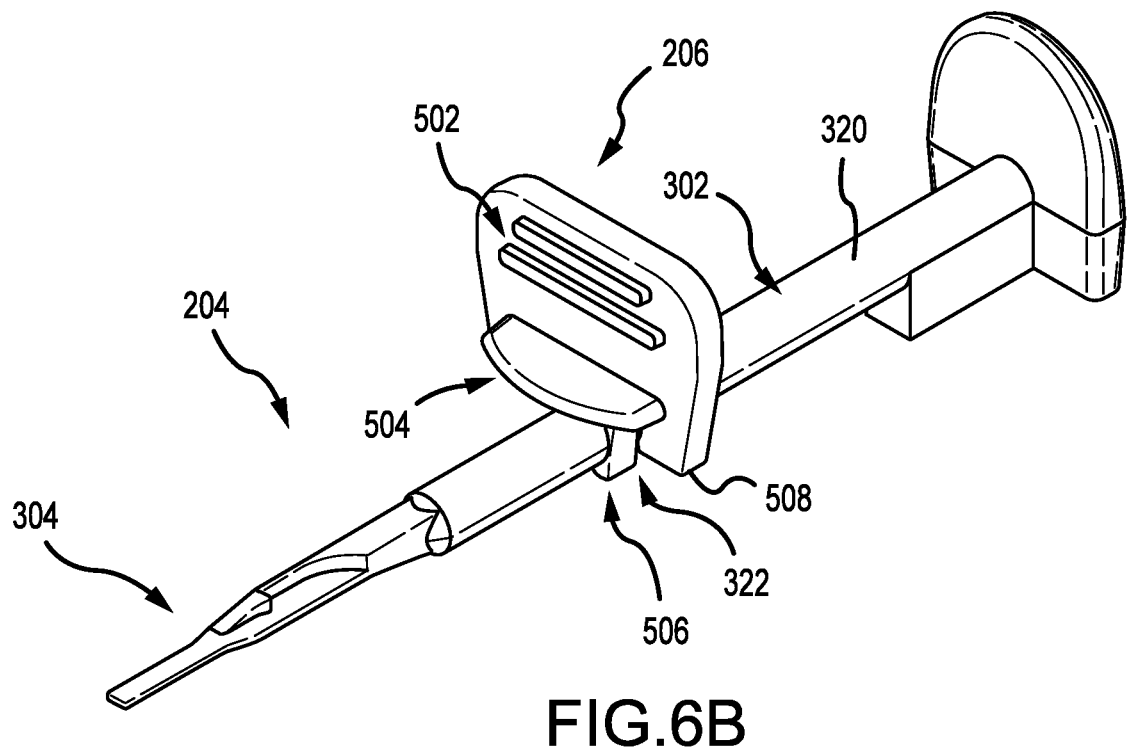

FIGS. 6A and 6B illustrate, respectively, a perspective view of the key 206 and the plunger 204 positioned apart from each other, and a perspective view of the key 206 coupled to the plunger 204. As illustrated in the figures, the fingers 506 of the key 206 can snap or be positioned around the elongated body 302 of the plunger 204 at the notches 322 of the shaft 320. When coupled thereto, the plunger 204 is inhibited from distal and proximal movement relative to the support base (not shown in FIGS. 6A and 6B) because the key 206 contacts the plunger guide (not shown).

Figure 7A:
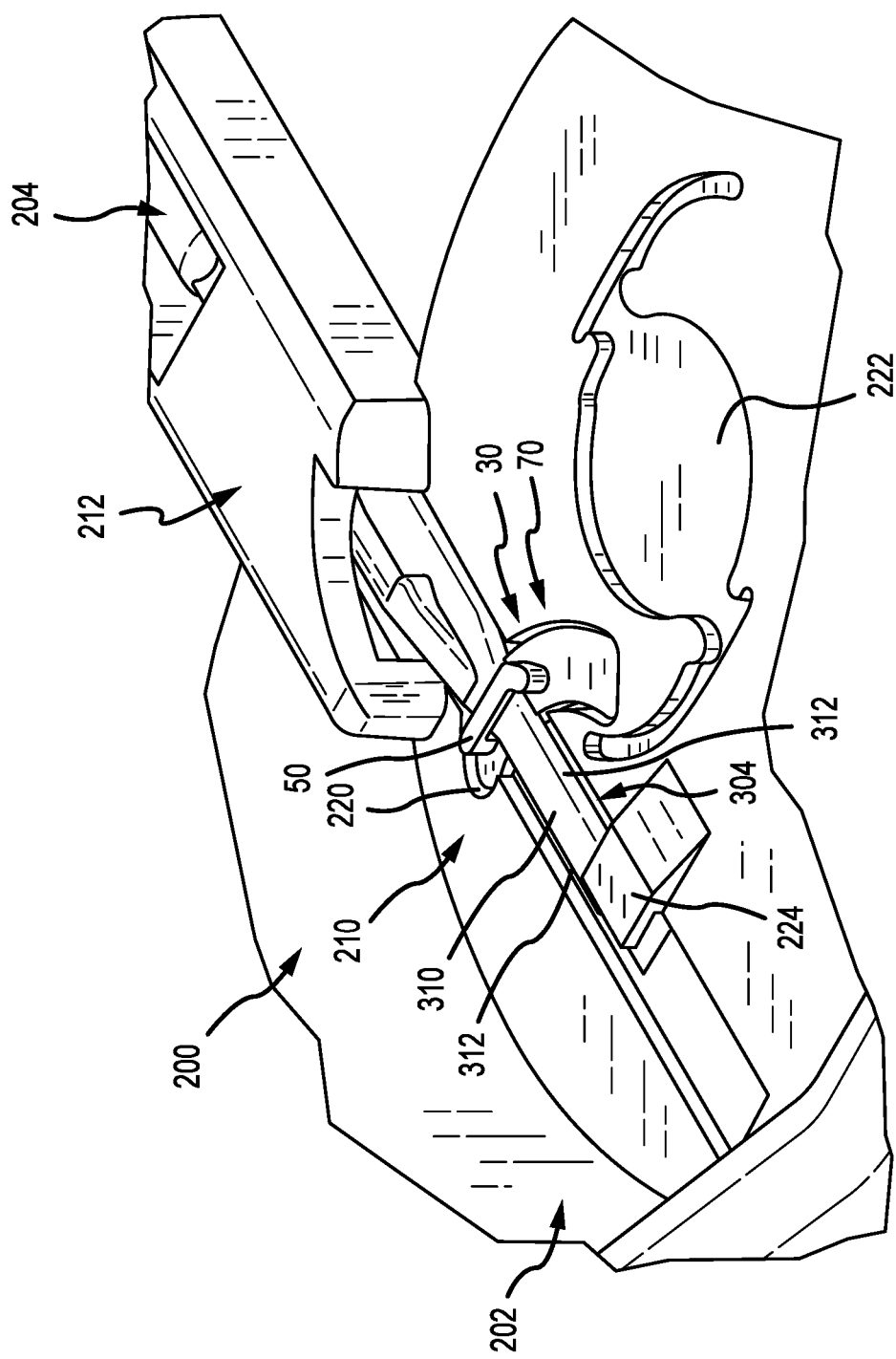
FIG. 7A illustrates a partial close-up view of a system of the disclosure, showing a plunger interfacing with a drug delivery component, in accordance with embodiments of the disclosure.

FIG. 7A illustrates a partial close-up view of the system 200 showing the plunger 204 interfacing with a drug delivery component 30. In certain embodiments, the plunger tip 304 is received through the fixation loop 50 of the drug delivery component 30, which has been inserted into the recess 220 of the first portion 210 of the support base 202 in a posterior-side up orientation exposing the fixation loop 50. The plunger tip 304 has also been received underneath the tab 224. In this state, which is suitable for packaging and shipping, the key (not shown in FIG. 7A) could be inserted into the opening of the plunger guide 212 or the plunger 204 could be oriented in the correct position to receive the key. In this state, the parallel side edges 312 and the generally planar top surface 310 of the plunger tip 304 are positioned through the fixation loop 50.

Figure 7B:
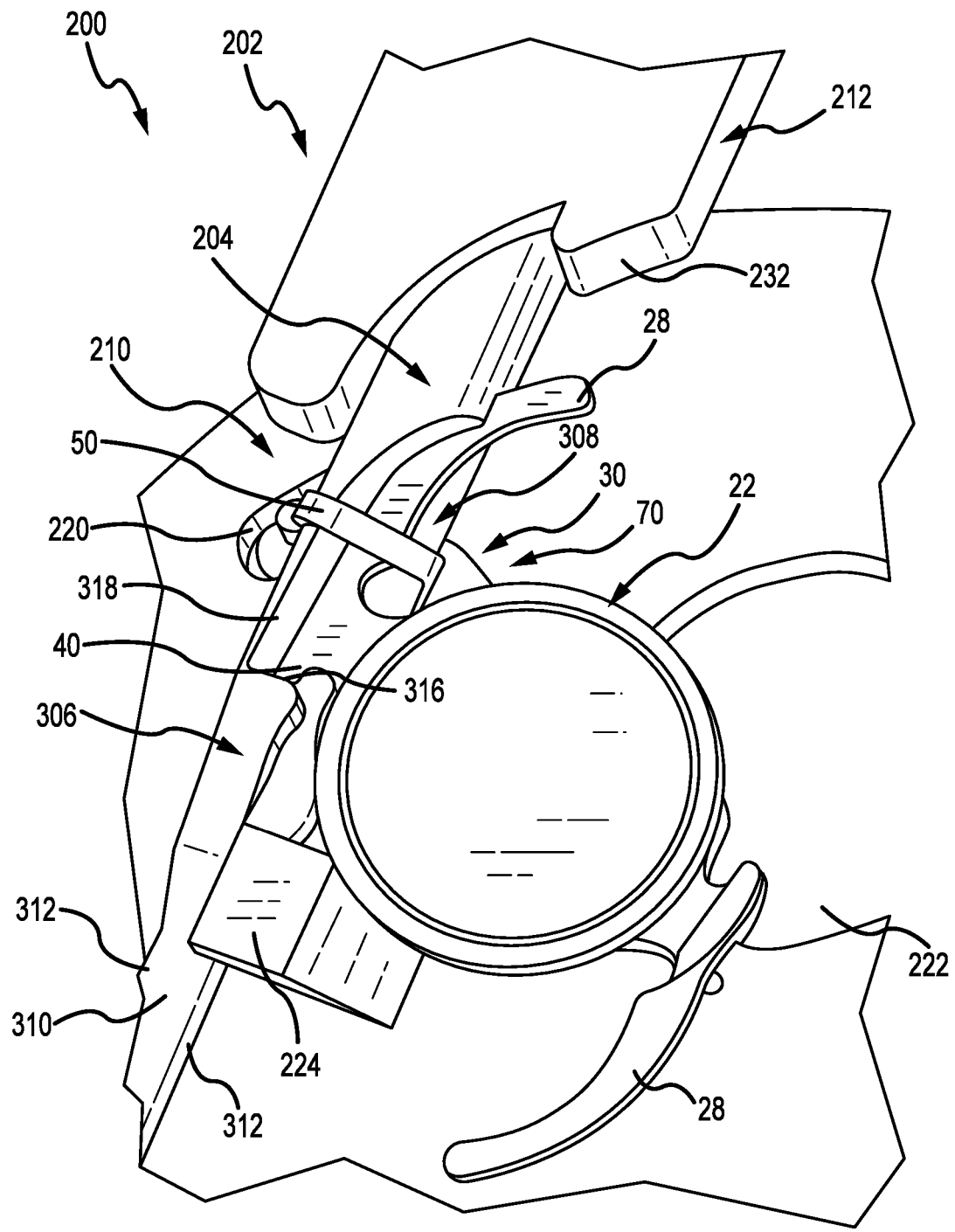
FIG. 7B illustrates a partial close-up view of a system of the disclosure, showing a haptic of an IOL assembly interfaced with a plunger and inserted through a fixation portion of a drug delivery component to affix the drug delivery component to the haptic of the IOL assembly, in accordance with embodiments of the disclosure.

FIG. 7B illustrates a partial close-up view of the system 200 showing a haptic 28 of an IOL assembly 22 interfaced with a plunger 204 and inserted through a fixation loop 50 of a drug delivery component 30 to affix the drug delivery component 30 to the haptic 28 of the IOL assembly 22. FIG. 7B illustrates the plunger 204 having been distally advanced or moved from its previous position in FIG. 7A. To do so, the key (not shown in FIG. 7B) would need to be removed from coupling with the plunger 204. Distal advancement of the plunger 204 from the state shown in FIG. 7A causes the fixation loop 50 to expand by the ramp 306 being wedged underneath the fixation loop 50. With sufficient distal advancement, the thin sidewall 318 extends the fixation loop 50 up and open over the compartment 308 so the haptic 28 can be fed through the fixation loop 50.

As illustrated in FIG. 7B, the retention tab 40 of the haptic 28 abuts the proximal surface 316 of the ramp 306. Opposite the retention tab 40, the free end of the haptic 28 is opposing the angled corner 232 such that retraction of the plunger 204 will cause the free end of the haptic 28 to contact the angled corner 232 of the plunger guide 212 and prevent the haptic 28 from moving proximally. As the plunger 204 moves proximally from the position shown in FIG. 7B, the fixation loop 50 will slide along the sidewall 318 and down the ramp 306, which will cause contraction of the fixation loop 50 (which is flexible). The free end of the haptic 28 will contact the angled corner 232 and the retention tab 40 will continue to be moved proximally since it is in contact with the proximal surface 316 of the ramp 306. Thus, the haptic 28 will be caused to rotate clockwise at least slightly as the fixation loop 50 is contracted onto the waist of the haptic 28.

The systems of the disclosure can be made in any suitable manner known in the art. By way of non-limiting example, the systems can be made using 3D printing, machine tooling, or can be molded from plastics. Any materials suitable for use in connection with ophthalmic surgical practices can be used. Further, the support base and the plunger can be formed from the same material or can be formed from different materials. The systems can be made for one-time, single use, or can be made for repeated use (e.g., they can be disposable, or can be made to be cleaned and sterilized between uses). By way of non-limiting example, the systems can be made from FDA approved and/or USP suitable polymers, e.g., Class VI polypropylene (PP-P5M6K-080), or can be made from FDA approved metal or metal alloys, e.g., stainless steel (SS316L). However, the disclosure is not so limited.

Figure 8:
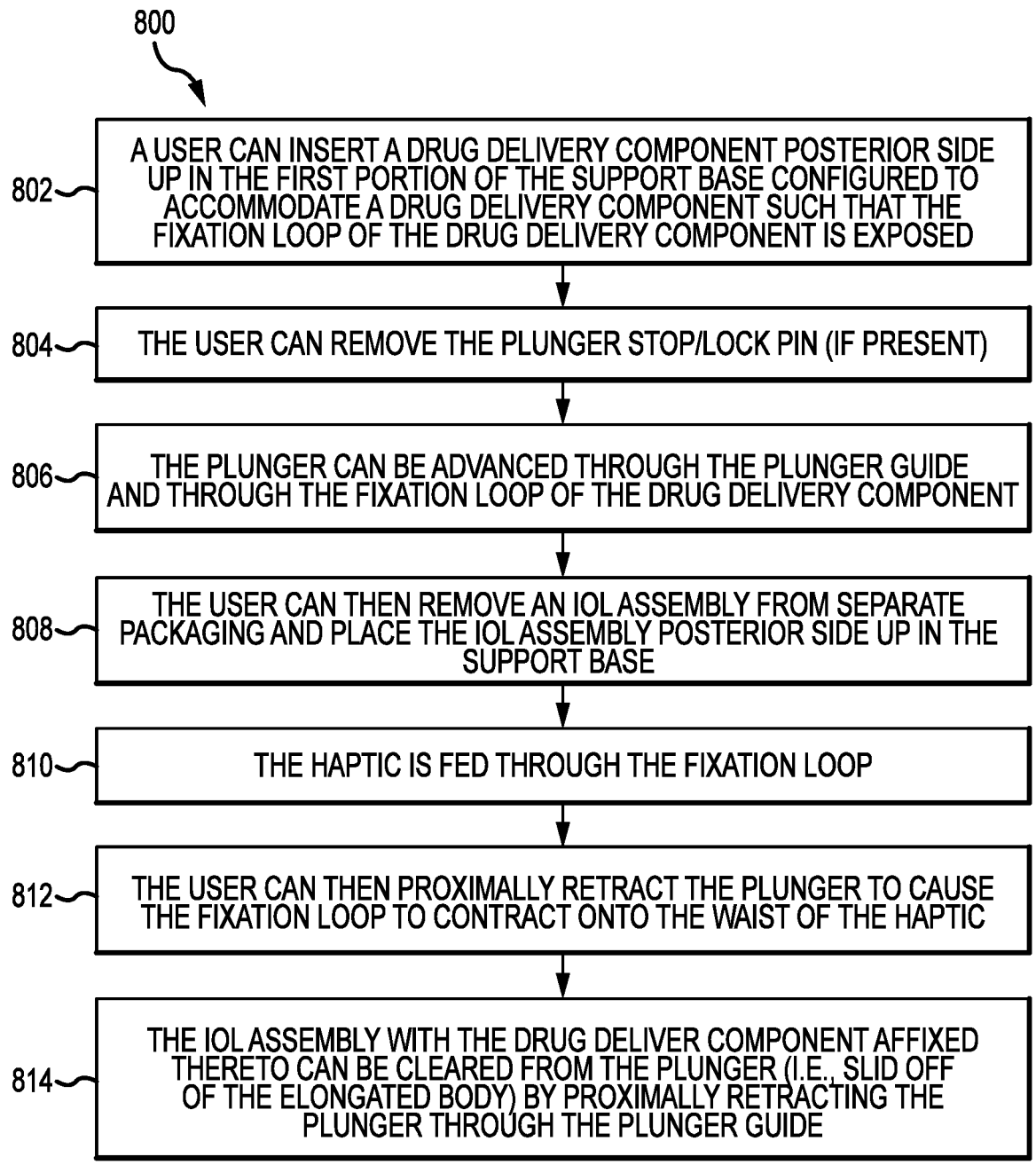
FIG. 8 is a flowchart showing an exemplary method of affixing a drug delivery component of an IOL assembly, in accordance with embodiments of the disclosure.

In certain embodiments, a drug delivery component can be affixed or secured to an IOL assembly utilizing a system of the disclosure in any suitable manner. By way of example, a method 800 of affixing a drug delivery component to an IOL assembly is provided in the flowchart of FIG. 8. At step 802, a user can insert a drug delivery component posterior side up in the first portion of the support base configured to accommodate a drug delivery component such that the fixation loop of the drug delivery component is exposed (see, e.g., FIG. 7A). At step 804, the user can remove the plunger stop/lock pin (if present). This can be done with one hand while the other hand holds the support base. At step 806, the plunger can be advanced through the plunger guide and through the fixation loop of the drug delivery component. One hand of the user can hold the support base, and with the other hand the user can activate (push/insert) the plunger to advance the plunger through the fixation loop of the drug delivery component until an initial resistance stop point is reached (see FIG. 7A). At step 808, the user can then remove an IOL assembly from separate packaging and place the IOL assembly posterior side up in the support base. At step 810, the haptic is fed through the fixation loop. This step may include using forceps or other suitable tool (e.g., Katalyst Surgical Fechtner Conjuctiva Forceps or equivalent) to gently grasp the leading haptic and feed the haptic into the fixation loop of the drug delivery component until the forceps can no longer feed the haptic through the fixation loop. At this point, at least part of the haptic is fed through the fixation loop, thereby allowing the user to pull on the tip of the haptic from the opposite side of the fixation loop. Using the forceps, the user can then gently grasp the tip of the haptic that has been fed through the fixation loop and pull the remaining section of haptic through the fixation loop until the end of the haptic seated against the ramp of the tip of the plunger to thereby secure the drug delivery component to the IOL assembly (see FIG. 7B). At step 812, the user can then proximally retract the plunger to cause the fixation loop to contract onto the waist of the haptic. At step 814, the IOL assembly with the drug delivery component affixed thereto can be cleared from the plunger (e.g., slide off the elongated body) by proximally retracting the plunger through the plunger guide. The steps can be repeated as needed to secure additional drug delivery components to any remaining haptics of the IOL assembly.

While the preferred embodiments of the devices and methods have been described in reference to the environment in which they were developed, they are merely illustrative of the principles of the inventions. The elements of the various embodiments can be incorporated into each of the other species to obtain the benefits of those elements in combination with such other species, and the various beneficial features can be employed in embodiments alone or in combination with each other. Other embodiments and configurations can be devised without departing from the spirit of the inventions and the scope of the appended claims.

What is claimed is:

1. A system for securing a drug delivery component to an intraocular lens (IOL) assembly, the drug delivery component comprising a therapeutic agent-containing portion and a fixation loop coupled to the therapeutic agent-containing portion, the IOL assembly including a haptic, the system comprising:
   a plunger and a support base, the plunger including an elongated body and a tip, the support base including a first portion and a second portion, the first portion configured for accommodating the drug delivery component, the second portion including a plunger guide configured for guiding movement of the plunger relative to the support base,
   wherein, when the drug delivery component is positioned at the first portion, the plunger is configured to be guided in distal movement by the plunger guide such that the tip is received in the fixation loop of the drug delivery component to secure the drug delivery component in a first state at the first portion.

2. The system of claim 1, wherein, upon the tip of the plunger being received in the fixation loop, additional distal movement of the plunger is configured to transition the fixation loop to a second state with the fixation loop being expanded.

3. The system of claim 2, wherein the tip of the plunger includes a top surface and a ramp extending upwards from the top surface, the ramp configured to expand the fixation loop of the drug delivery component during distal movement into the second state.

4. The system of claim 3, wherein the ramp includes a proximal surface, the tip of the plunger further including a sidewall extending proximally from the proximal surface of the ramp, wherein the proximal surface of the ramp, the sidewall, and the top surface of the tip of the plunger define a compartment for receiving the haptic of the IOL assembly therein and the haptic of the IOL assembly is configured to go through the fixation loop in the second state.

5. The system of claim 4, wherein, when the haptic of the IOL assembly is received in the compartment, proximal retraction of the plunger is configured to transition the fixation loop to a third state with the fixation loop being contracted onto the haptic of the IOL assembly.

6. The system of claim 1, wherein the first portion includes a recess sized and shaped to receive the therapeutic agent-containing portion of the drug delivery component therein.

7. The system of claim 1, wherein the first portion includes an IOL recess sized and shaped to receive the IOL assembly therein.

8. The system of claim 1, wherein the plunger guide includes a passageway or channel for guiding movement of the plunger.

9. The system of claim 1, further including a key lock configured to interface with the plunger to inhibit movement within the plunger guide.

10. The system of claim 1, further comprising the drug delivery component.

11. A kit comprising: the system of claim 1; and at least one container.

12. A system for securing a drug delivery component to an intraocular lens (IOL) assembly, the drug delivery component including a therapeutic agent-containing portion and a fixation loop coupled to the therapeutic agent-containing portion, the IOL assembly including a haptic, the system comprising:

a support base and a plunger, the support base including a plunger guide and a recess, the recess being sized and shaped to receive the therapeutic agent-containing portion of the drug delivery component therein in a posterior-side up orientation, the plunger guide configured for guiding movement of the plunger relative to the support base along an axis that intersects the recess, wherein, when the therapeutic agent-containing portion is received in the recess, the plunger is configured to be guided in distal movement by the plunger guide such that a tip of the plunger is received in the fixation loop of the drug delivery component.

13. The system of claim 12, wherein the tip of the plunger includes a ramp and a sidewall extending proximally from the ramp.

14. The system of claim 13, wherein a compartment is formed by a proximal surface of the ramp and an inner surface of the sidewall, the compartment sized and shaped to receive a portion of the haptic therein.

15. The system of claim 12, wherein, in the posterior-side up orientation of the drug delivery component, the fixation loop is exposed.

16. The system of claim 12, wherein, upon the tip of the plunger being received in the fixation loop of the drug delivery component, additional distal movement of the plunger is configured to expand the fixation loop for receiving the haptic of the IOL assembly therethrough.

17. The system of claim 12, further comprising the drug delivery component.

18. A kit comprising: the system of claim 12; and at least one container.

19. The kit of claim 18, further comprising an instruction guide.

20. The kit of claim 18, wherein the kit does not include an IOL.

* * * * *